US00PP34222P2

(12) United States Plant Patent
Li

(10) Patent No.: US PP34,222 P2
(45) Date of Patent: May 10, 2022

(54) ***VERBENA* PLANT NAMED 'KLEVP20067'**

(50) Latin Name: ***Verbena* x *hybrida***
Varietal Denomination: KLEVP20067

(71) Applicant: Klemm+Sohn GmbH & Co. KG, Stuttgart (DE)

(72) Inventor: Ruijun Li, North Parramatta (AU)

(73) Assignee: KLEMM+SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 17/331,282

(22) Filed: May 26, 2021

(51) Int. Cl.
*A01H 5/02* (2018.01)
*A01H 6/86* (2018.01)

(52) U.S. Cl.
USPC ..... Plt./308
CPC ..... *A01H 6/86* (2018.05)

(58) Field of Classification Search
USPC ..... Plt./308
CPC ..... A01H 6/86; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Verbena* plant particularly distinguished by red flowers and excellent branching, is disclosed.

1 Drawing Sheet

Genus and species: *Verbena* x *hybrida*.
Variety denomination: 'KLEVP20067'.

BACKGROUND OF THE NEW PLANT

The present invention comprises a new and distinct variety of *Verbena*, botanically known as *Verbena* x *hybrida*, and hereinafter referred to by the variety name 'KLEVP20067'. 'KLEVP20067' originated from a cross-pollination conducted in November 2015 in Cobbitty, New South Wales, Australia between the proprietary female *Verbena* variety '12.0048' (unpatented), and the proprietary male *Verbena* variety '08.0087' (unpatented).

The seeds from the cross were sown and plants were grown for evaluation, where an individual plant designated 'KLEVP20067' was selected from the group of plants in Cobbitty, New South Wales, Australia in October 2016.

In October 2016, 'KLEVP20067' was first vegetatively propagated by vegetative cuttings in Cobbitty, New South Wales, Australia. 'KLEVP20067' was found to reproduce true to type in successive generations of asexual propagation via vegetative stem cuttings.

SUMMARY

The following are the most outstanding and distinguishing characteristics of this new variety when grown under normal horticultural practices in Cobbitty, New South Wales, Australia.

1. Red flowers; and
2. Excellent branching.

DESCRIPTION OF THE PHOTOGRAPH

This new *Verbena* plant is illustrated by the accompanying photograph which shows the plant's foliage, and flowers. The photograph is of a plant approximately twelve weeks old grown indoors in Stuttgart, Germany in April 2020. The colors shown are as true as can be reasonably obtained by conventional photographic procedures.

DESCRIPTION OF THE NEW VARIETY

The following detailed descriptions set forth the distinctive characteristics of 'KLEVP20067'. The data which define these characteristics were collected from asexual reproductions carried out in Latina, Italy. Data was collected on three-month-old plants grown in a greenhouse in Latina, Italy in 2019. Color references are to The R.H.S. Colour Chart of The Royal Horticultural Society of London (R.H.S.), 5$^{th}$ edition (2007).

Classification:
- *Family.*—Verbenaceae.
- *Botanical.*—*Verbena* x *hybrida.*
- *Common.*—*Verbena.*
- *Designation.*—'KLEVP20067'.

Parentage:
- *Female parent.*—'12.0048' (unpatented).
- *Male parent.*—'08.0087' (unpatented).

Plant:
- *Growth and branching habit.*—Upright with compact round shape.
- *Height* (*from top of soil*).—20.5 cm.
- *Width* (*horizontal plant diameter*).—39.0 cm.
- *Time to produce a finished flowering plant.*—Approximately 8 weeks.
- *Time to initiate and develop roots.*—2 weeks.
- *Root description.*—White, RHS 155B, fine and fibrous roots.

Stems:
- *Number of branches per plant.*—More than 25.
- *Length.*—22.0 cm.
- *Diameter.*—0.26 cm.
- *Internode length.*—Approximately 2.1 cm.
- *Color.*—RHS 139D.
- *Anthocyanin.*—Absent.
- *Texture and appearance.*—Pubescent, round.

Leaves:
*Arrangement.*—Opposite.
*Immature and mature leaf color.*—Upper surface: RHS 141A. Lower surface: RHS 141C.
*Length.*—4.4 cm.
*Width.*—2.2 cm.
*Shape.*—Lanceolate.
*Apex.*—Acute.
*Base.*—Obtuse.
*Margin.*—Crenate.
*Division.*—Absent.
*Texture.*—Upper surface: Leathery. Lower surface: Rugose.
*Venation type.*—Pinnate.
*Venation color* (*both upper and lower surfaces*).—RHS 141D.
*Petioles.*—Length: 0.2 cm. Diameter: 0.1 cm. Color: RHS 141D. Texture: Leathery.

Flower buds:
*Shape.*—Tall, cylindrical.
*Length.*—1.3 cm.
*Diameter.*—0.3 cm.
*Color* (*at tight bud*).—RHS 40B.

Inflorescence:
*Inflorescence in profile.*—Broad ovate.
*Blooming habit* (*flowering season*).—Continuously.
*Lastingness of individual blooms on the plant.*—About 1 week.
*Fragrance.*—Absent.
*Inflorescence type.*—Umbel.
*Length of inflorescence.*—3.5 cm.
*Diameter of inflorescence.*—4.8 cm.
*Number of florets per inflorescence.*—Average of 22.
*Peduncle.*—Color: RHS 141A. Length: 2.4 cm. Diameter: 0.2 cm.

Florets:
*Length.*—1.8 cm.
*Diameter.*—2.1 cm.
*Texture.*—Smooth.
*Form.*—Single.
*Color.*—Immature: Upper surface: RHS 41A. Lower surface: RHS N155D. Mature: Upper surface: when opening, RHS 41B; then outside part fading to RHS 52B. Lower surface: RHS N155D.
*Corolla tube length.*—1.5 cm.
*Corolla tube color.*—RHS 157B.
*Arrangement of corolla lobes.*—Touching.
*Curvature of the longitudinal axis of the corolla lobe.*—Straight.
*Corolla eye.*—No eye, tiny dark center at throat opening, RHS N187A.
*Petals.*—Length of lobe: 1.2 cm. Diameter of lobe: 0.8 cm. Lobe shape: Obtuse. Apex: Emarginate. Margin: Entire. Texture (both upper and lower surfaces): Smooth, glabrous.
*Pedicels.*—Not visible.

Sepals:
*Shape.*—Lanceolate but fused.
*Apex.*—Acute.
*Margin.*—Entire.
*Length.*—1.0 cm.
*Diameter.*—0.2 cm.
*Color.*—RHS 141C.
*Texture* (*both upper and lower surfaces*).—Hairy, dull.

Reproductive organs:
*Stamens.*—Present. Quantity: 4. Appearance: Didynamous. Color: RHS 139D. Filament length: 0.3 cm. Filament diameter: 0.1 cm.
*Anther.*—Shape: Elliptic. Color: RHS 141D. Length: 0.2 cm. Diameter: 0.1 cm.
*Pollen amount.*—Sparse.
*Pollen color.*—RHS 2D.
*Pistils.*—Quantity: 1. Length: 1.4 cm. Diameter: 0.1 cm. Stigma: Color: RHS 141D. Appearance: Ovate. Length: 0.1 cm. Diameter: 0.1 cm. Style: Color: RHS 141D. Length: 1.2 cm. Diameter: 0.1 cm. Appearance: Long.

Fruit and seed set: None observed.

Disease and pest/insect resistance: Good tolerance to powdery mildew (*Podosphaera xanthii*).

COMPARISON WITH PARENTAL LINES AND KNOWN VARIETY

'KLEVP20067' is distinguished from its parents as described in Table 1.

TABLE 1

Comparison with Parental Lines

| Characteristic | 'KLEVP20067' | Female parent | Male parent |
|---|---|---|---|
| Flower color | Red | Red with tiny white eye | Red |
| Flower size | Medium | Slightly bigger than KLEVP20067 | Smaller than KLEVP20067 |
| Branching | Excellent | Average | Excellent |

'KLEVP20067' is most similar to the commercial *Verbena* Vepita Dark Red (not patented). Differences between the varieties are described in Table 2.

TABLE 2

Comparison with Similar Variety

| Trait | Variety 'KLEVP20067" | Commercial line Vepita Dark Red |
|---|---|---|
| Flower color | Red with tiny dark center | Red with white hairs on throat |
| Teeth on Leaf margin | Shorter than Vepita Dark Red | Longer than KLEVP20067 |
| Earliness | Earlier than Vepita Dark Red | Later than KLEVP20067 |

I claim:

1. A new and distinct cultivar of *Verbena* Plant Named 'KLEVP20067' as described and illustrated herein.

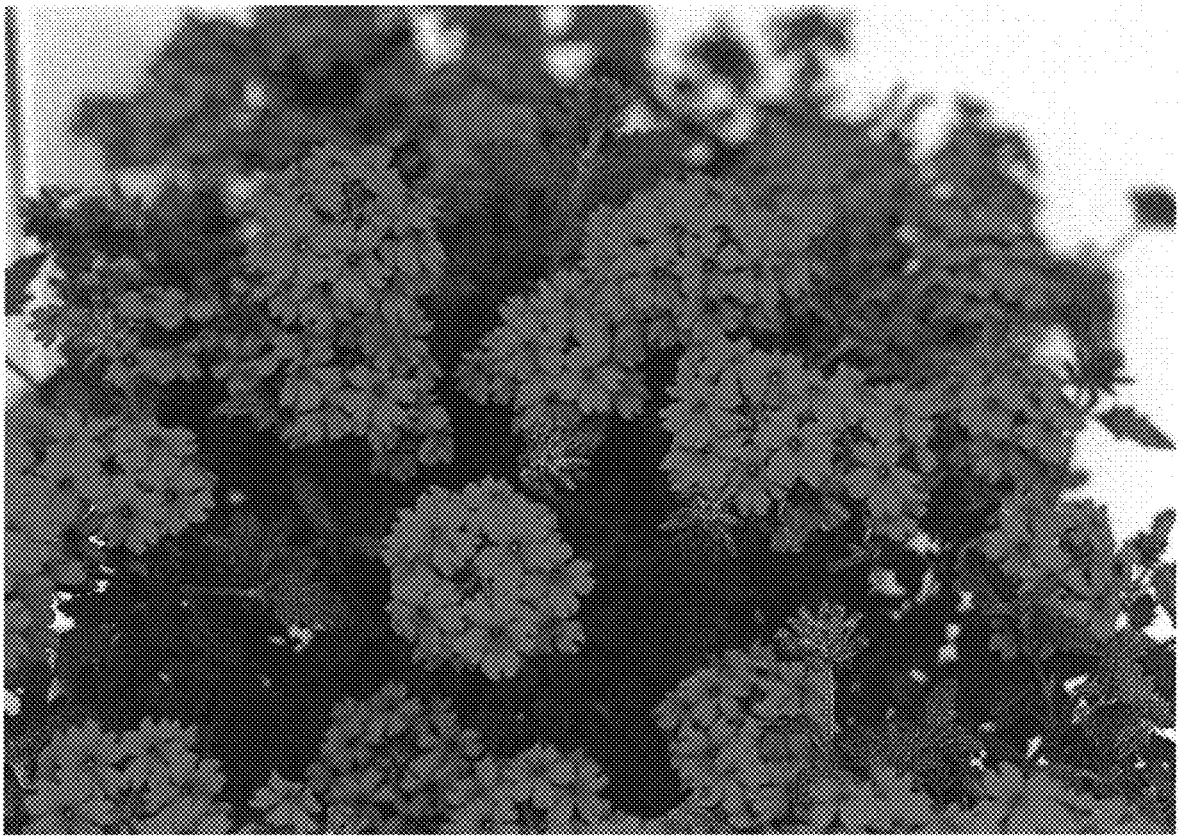

* * * * *